United States Patent
Grziwotz et al.

(10) Patent No.: US 8,234,938 B2
(45) Date of Patent: Aug. 7, 2012

(54) ARRANGEMENT AND METHOD FOR THE AUTOMATIC SAMPLING IN A STORAGE TANK SYSTEM INTERCONNECTED TO A PIPE SYSTEM FOR SUPPLYING CLEANING FLUIDS

(75) Inventors: Leo Grziwotz, Oststeinbek (DE); Uwe Sobottka, Mölln (DE); Arno Peter, Büchen (DE)

(73) Assignee: GEA Brewery Systems GmbH, Kitzingen (DE)

( * ) Notice: Subject to any disclaimer, the term of this patent is extended or adjusted under 35 U.S.C. 154(b) by 550 days.

(21) Appl. No.: 12/519,399

(22) PCT Filed: Nov. 5, 2007

(86) PCT No.: PCT/EP2007/009562
§ 371 (c)(1),
(2), (4) Date: Jun. 16, 2009

(87) PCT Pub. No.: WO2008/074377
PCT Pub. Date: Jun. 26, 2008

(65) Prior Publication Data
US 2010/0018329 A1   Jan. 28, 2010

(30) Foreign Application Priority Data
Dec. 16, 2006   (DE) .......................... 10 2006 059 556

(51) Int. Cl.
*G01N 1/20* (2006.01)
(52) U.S. Cl. .................................................. 73/863.02
(58) Field of Classification Search ................ 73/863.02
See application file for complete search history.

(56) References Cited

U.S. PATENT DOCUMENTS
3,524,351 A   8/1970   Bayly et al.
(Continued)

FOREIGN PATENT DOCUMENTS
DE   4332386 A1   3/1995
(Continued)

OTHER PUBLICATIONS

GEA Process Equipment Division Brochure "Varivent Valves," Tuchenhagen GmbH, May 2006, 32 pgs.
(Continued)

*Primary Examiner* — Hezron E Williams
*Assistant Examiner* — Rodney T Frank
(74) *Attorney, Agent, or Firm* — Fredrikson & Byron, PA (57) ABSTRACT

The invention pertains to an arrangement and a method for the automatic sampling in a storage tank system (1) interconnected to a pipe system (4) for supplying cleaning fluids, particularly in processing systems that are subject to high microbiological quality requirements in the food and beverage industry, particularly in breweries, with a storage tank system (1) that consists of several tanks and a sampling device (5) that is respectively associated with all tanks via permanent pipework. The invention ensures that the entire sampling system including all valves integrated therein can be cleaned and sterilized in a flow-through fashion regardless of the respective content of the tanks. Furthermore, the sampling should take place without a loss of the fluid to be sampled. This is procedurally achieved in that a volume flow Q(P) of the fluid (P) to be sampled is diverted from a selected tank (1.*i*), wherein this volume flow Q(P) is fed to the sampling device (5) and is returned from the sampling device into the selected tank (1.*i*), and wherein a quality control of the fluid (P) to be sampled is carried out in a flow-through fashion and/or a sample quantity (PR) of the fluid (P) is diverted from the volume flow Q(P) within the sampling device (5) during the circulation of the volume flow Q(P).

15 Claims, 7 Drawing Sheets

U.S. PATENT DOCUMENTS

| | | |
|---|---|---|
| 4,993,271 A | 2/1991 | Vargason |
| 5,469,751 A | 11/1995 | Weiss et al. |
| 6,637,277 B2 | 10/2003 | Gamache et al. |
| 6,764,651 B2 | 7/2004 | Fernando et al. |
| 6,923,076 B2 | 8/2005 | Carlson |
| 7,028,563 B2 | 4/2006 | Gamache et al. |
| 2002/0129668 A1 | 9/2002 | Gamache et al. |
| 2005/0217351 A1 | 10/2005 | Kreck et al. |

FOREIGN PATENT DOCUMENTS

| | | |
|---|---|---|
| DE | 19822424 A1 | 7/1999 |
| DE | 102004062166 A1 | 6/2006 |

OTHER PUBLICATIONS

GEA Tuchenhagen GmbH Brochure "About Us," Feb. 2006, 24 pgs.
GEA Spare Parts List, Tuchenhagen GmbH, Aug. 16, 2006, 2 pgs.
"PCT International Search Report dated Feb. 27, 2008 for PCT/EP2007/009562, from which the instant application is based," 3 pgs.

ARRANGEMENT AND METHOD FOR THE AUTOMATIC SAMPLING IN A STORAGE TANK SYSTEM INTERCONNECTED TO A PIPE SYSTEM FOR SUPPLYING CLEANING FLUIDS

RELATED APPLICATIONS

This application is a 35 U.S.C. 371 national stage filing from International Application No. PCT/EP2007/009562 filed Nov. 5, 2007, which claims priority to German Patent Application No. 10 2006 059 556.4, filed Dec. 16, 2006, the teachings of which are incorporated herein by reference.

TECHNICAL FIELD

The invention pertains to an arrangement and a method for the automatic sampling in a storage tank system interconnected to a pipe system for supplying cleaning fluids, especially in processing systems for processing and transferring products in the food and beverage industry that are subject to high microbiological quality requirements, particularly in breweries, with a storage tank system that consists of several tanks and a sampling device that is respectively associated with all tanks via permanent pipework.

STATE OF THE ART

The pertinent state of the art in the food and beverage industry, particularly in breweries, is characterized in that a manually or automatically actuated sampling valve is arranged on each tank in the suitable region to be considered. These sampling valves are usually associated with a centrally arranged sampling device via permanent pipework, and the fluid to be sampled (product) that is diverted from the tank by means of the sampling valve is fed to the sampling device via the respective pipework. In the sampling device, the fluid to be sampled is either analyzed on the spot in a flow-through fashion (for example, density determination or $O_2$- or $CO_2$-concentration) or a certain sample quantity of the fluid to be sampled is filled into a sample container, the content of which can then be analyzed under laboratory conditions at a different location.

Prior to diverting the fluid to be sampled from the respectively selected tank, the entire sampling system exposed to this fluid including the sampling valve needs to be subjected to a cleaning and sterilizing process. This is achieved in that, during the cleaning of a tank, the sampling system assigned to this tank is also cleaned and, if applicable, sterilized by means of a cleaning circuit extending through the tank. The cleaning and sterilizing of the sampling system including the sampling valve can usually not be carried out while the tank is exposed to the product because this would require the opening of the sampling valve toward the interior of the tank in order to clean its valve seat surface. Another disadvantage of this sampling method can be seen in that the diverted fluid to be sampled minus the actual sample quantity is not returned into the process, but rather discarded. The discarding of the aforementioned fluid may have an environmental impact or represent an undesirable material loss when sampling products of high value.

However, there also exist simple solutions, in which the respective sampling valve arranged on the tank is not connected to further pipework, but rather merely features a controllable drain sleeve for withdrawing a certain sample quantity into a sample container. The drain sleeve can be scorched in order to be sterilized. The regions of the sampling valve that come in contact with the sample quantity are cleaned and sterilized parallel to the aforementioned tank cleaning, wherein the corresponding quantity of cleaning medium is discarded because it needs to pass the valve seat surface. With the exception of the product losses during the sampling that are minimal at best in the present instance, this sampling method has the same disadvantages as the above-described permanent pipework between a plurality of sampling valves and a central sampling device.

U.S. Pat. No. 6,637,277 B2 already discloses a sampling system with sample feed and return lines, with a common closed circular pipeline for all sampling points that serves for withdrawing the sample into an analyzing system, wherein the mediums to be sampled preferably consist of gaseous fluids, and with measures for flushing the sampling system with the medium to be sampled. Similar systems are also known from U.S. Pat. No. 7,028,563 B2 and U.S. Pat. No. 5,469,751.

U.S. Pat. No. 4,993,271 discloses an automatic sampling and analyzing method, wherein the samples are respectively obtained from one container of a container system that consists of several containers and are returned into the original container after the analysis. Similar methods are known from DE 43 32 386 A1, U.S. Pat. No. 6,764,651 B2, U.S. Pat. No. 6,923,076 B2 and DE 10 2004 062 166 A1.

The present invention aims to develop an automatic sampling arrangement and a corresponding method of the initially described type, in which the entire sampling system including all integrated valves that is exposed to the fluid to be sampled during the course of any sampling can be cleaned and sterilized in a flow-through fashion regardless of the respective content of the tanks. Furthermore, the sampling should take place without noteworthy loss of the fluid to be sampled.

SUMMARY OF THE INVENTION

This objective is attained with an arrangement with the characteristic of claim 1. Advantageous embodiments of the proposed arrangement form the objects of the dependent claims. A method for the automatic sampling in a storage tank system interconnected to a pipe system for supplying cleaning fluids that can be carried out by means of an automatic sampling arrangement with the characteristics of claim 1 is defined by the characteristics of claim 10. Advantageous variations of the method form the objects of the dependent claims.

The proposed inventive arrangement and the inventive method provide the following advantages:

The feed valves that divert the fluid to be sampled from the tank and the return valves that return the fluid to be sampled into this tank can be automatically actuated, are designed in a double-sealing and mix-proof fashion and feature valve seats that can be cleaned.

A sampling that is representative for the tank content can be realized on each tank automatically by means of the central sampling device and also manually.

Quality controls of the fluid to be sampled can be realized in a flow-through fashion in the central sampling device.

The entire sampling system including the feed and return valves with their relevant valve seat surfaces can be cleaned and sterilized in a flow-through fashion.

The sampling takes place without noteworthy loss of the fluid to be sampled. During the course of the sampling, the loss is limited to the quantities that need to be ordinarily provided for the return into the tank for safety reasons during the ejection of the sampled fluid by means of desalinated water because the fluid changeover is not highly selective.

The proposed sampling by means of the central sampling device can be applied to a plurality of tanks, for example, ten in number.

One decisive aspect of the inventive solution consists of the arrangement of two valves on each tank in the lower region thereof, namely a feed valve and a return valve that are positioned a certain distance from one another, are designed in a double-sealing fashion in the respective valve seat region, as well as in a mix-proof fashion, and feature valve seats that can be cleaned. The valves comprise a through-housing with a first and a second connecting sleeve and a tank connection that is connected to the interior of the respectively assigned tank and can be switched by means of the assigned valve.

According to another essential aspect of the inventive solution, the tanks are respectively connected to one another in series by means of the feed line extending through the respective connecting sleeves of the feed valves and by means of the return line extending through the respective connecting sleeves of the return valves, wherein the feed line and the return line are connected to one another by means of a sampling device on their end that lies opposite of the pipe system for supplying cleaning fluids and form a closed circular pipeline.

According to a third essential aspect of the solution, it is proposed that shut-off valves are respectively provided at certain locations in the feed line and in the return line, wherein these shut-off valves make it possible to select a certain tank for sampling, to divert a volume flow of the fluid to be sampled from the tank, to circulate this volume flow through the sampling device and to subsequently return the volume flow into the tank under hygienically optimal conditions in connection with the respective feed valve and return valve on the tank according to the first aforementioned aspect of the solution and in connection with the serial interconnection between the tanks according to the second aforementioned aspect of the solution. This furthermore makes it possible to carry out the sampling without noteworthy loss of the fluid to be sampled. In addition, all relevant regions of the entire sampling system including the feed and return valves arranged on the respective tank can be cleaned and sterilized in a flow-through fashion.

With respect to the design of the feed and return valves, the invention proposes either a so-called double-seat valve or a so-called double-seal valve. A double-seat valve is known, for example, from the company brochure GEA Tuchenhagen, VARIVENT® Valves, 610d-05/06 and is referred to as VARIVENT® double-seat tank bottom valve Type T . . . therein. One variation that is particularly suitable for the proposed automatic sampling arrangement is shown in the replacement parts list of the aforementioned manufacturer for a so-called double-seat bottom valve T_RC, 221ELI004791G_0.doc that is dated Aug. 16, 2006. Another reference to a double-seat valve suitable for this purpose can be found in the company publication "über UNS" of the aforementioned manufacturer, namely on page 4 of Edition 2—2006 that shows an illustration entitled VARIVENT® double-seat bottom valve DN25, 1" OD with lift function.

As far as the only double-sealing closing element and its partial strokes for ensuring a valve seat cleaning are concerned, the basic design of the proposed double-seal valve is known, for example, from DE 198 22 424 C2. In the embodiment that is illustrated in this publication and features a stepped housing consisting of two housing parts and a connecting opening that connects the two housing parts and can be controlled by the valve closing element, however, the known double-seal valve is not yet suitable for being connected to a tank as part of the inventive arrangement.

In order to clean and sterilize the inventive arrangement in a flow-through fashion and to realize the required ejections of the sampled fluid with desalinated water, as well as the flooding of the entire sampling system with desalinated water or sterile air, it is furthermore proposed that the pipe system for supplying cleaning fluids, which is respectively connected to the storage tank system via the feed line and the return line, features a first line for supplying a cleaning medium, a second line for carrying off the cleaning medium, a third line for supplying desalinated water, a fourth line for supplying steam or hot water and a fifth line for supplying sterile air.

According to another proposal, a conveying device, preferably a centrifugal pump, and a sampling valve are arranged in the sampling device referred to the flow direction. The latter makes it possible to divert a discrete sample quantity from the circulating volume flow of the fluid to be sampled, for example, into a sample bottle.

According to one advantageous embodiment of the sampling device, it is proposed that a flowmeter and a quality control device are arranged between the conveying device and the sampling valve referred to the flow direction. The flowmeter makes it possible to control the required ejections from the pertinent pipeline sections of relatively small nominal width very precisely and therefore without noteworthy product loss. The quality control device makes it possible to carry out a flow-through analysis of the fluid to be sampled on the spot. If the inventive arrangement is used within a brewery, the analysis could comprise, for example, a density determination and/or a determination of the $O_2$- and/or $CO_2$-concentration of the product.

The representativity of the obtained sample is promoted if the feed valve and the respectively assigned return valve, which need to be arranged at a sufficient distance from one another, are furthermore positioned at the same height in the region of the cylindrical surface area or in the upper region of the conical bottom section of the corresponding tank. This prevents cooler sludge particles that have sedimented in the tank cone from being whirled up, particularly in the region of the return valve.

According to another proposal, a short circuit between the diverted and the returned volume flow of the fluid to be sampled is effectively prevented if the feed valve and the respectively assigned return valve are arranged relative to one another at an angle of $90 \leq \alpha \leq 180$ degrees, preferably at $\alpha = 120$ degrees, referred to a plane extending perpendicular to the longitudinal axis of the tank.

According to one advantageous embodiment, a manual sampling can be realized in a surprisingly simple fashion with the proposed double-seat or double-seal valve due to the fact that a connecting path between the leakage cavity of the feed valve and its surroundings is designed for obtaining a manual sample.

The inventive automatic sampling arrangement makes it possible to realize a method for the automatic sampling in a storage tank system interconnected to a pipe system for supplying cleaning fluids that provides the above-described advantages and has the following characteristics:

A volume flow of the fluid to be sampled is automatically diverted from a selected tank at a first location, this volume flow is fed to the sampling device and returned into the selected tank from the sampling device at a second location, and a quality control of the fluid to be sampled is carried out in a flow-through fashion and/or a sample quantity of the fluid is diverted from the volume flow within the sampling device during the circulation of the volume flow from the first to the second location.

The connection of the proposed arrangement for the automatic sampling in a storage tank system to a pipe system for supplying cleaning fluids by means of a feed line and a return line allows the realization of an advantageous additional development of the method that makes it possible to clean and/or sterilize and to flood the entire sampling system with suitable fluids. According to this additional development, the entire sampling system that is exposed to the fluid to be sampled during the course of any sampling is cleaned with a cleaning medium in a flow-through fashion or sterilized with steam or hot water in a flow-through fashion or completely flooded with desalinated water or with sterile air prior to the respective sampling of one of the tanks regardless of the respective content of the tanks, wherein these fluids are supplied via the pipe system.

According to another advantageous embodiment of the proposed method, a representative sampling without adulteration of the fluid to be sampled with residual quantities of desalinated water or other fluids that have remained in the sampling system is ensured due to the fact that the desalinated water or other fluid situated in the assigned region for the circulation of the volume flow of the fluid to be sampled is ejected out of this region into the pipe system by means of the fluid to be sampled prior to the respective sampling of one of the selected tanks, wherein the fluid to be sampled is diverted from the tank to be sampled at the first location.

The losses of sampled fluid during the course of the sampling are reduced to an insignificant amount if the proposed method is additionally developed in such a way that the sampled fluid situated in the assigned region for the circulation of the volume flow of the sampled fluid is completely ejected out of this region into the sampled tank by means of the desalinated water at the second location subsequent to the respective sampling of one of the selected tanks.

The ejections of the desalinated water or the sampled fluid can be very precisely controlled in interaction with the pertinent pipeline sections that preferably have a relatively small nominal width if a flowmeter is provided in the region of the circulating volume flow and if this flowmeter controls the respective ejection.

BRIEF DESCRIPTION OF THE DRAWINGS

One embodiment of the proposed arrangement for the automatic sampling in a storage tank system according to the invention is illustrated in the drawings and is described below with respect to its design and operation.

In these drawings.

DETAILED DESCRIPTION

Figure 1:
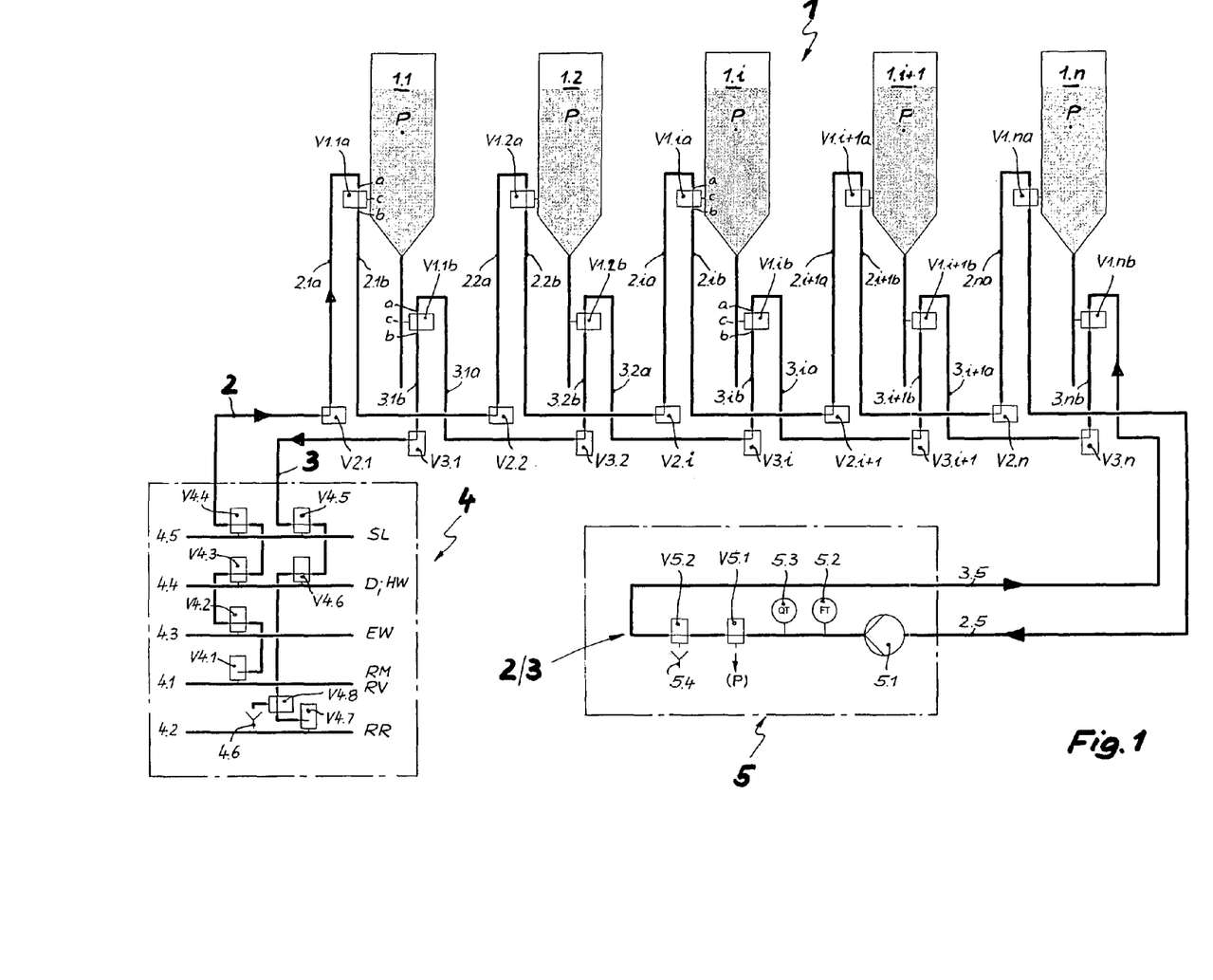
FIG. 1 shows a schematic representation of an inventive arrangement with, for example, five tanks that are interconnected to a pipe system for supplying cleaning fluids on the one hand and to a sampling device on the other hand.

FIG. 1 shows a storage tank system 1 that in the most general instance may consist of n tanks, namely the tanks 1.1 to 1.n. In order to prevent the length of the pipes leading to a central sampling device 5 from becoming excessively long, the maximum number of tanks assigned to a sampling device 5 should be limited to approximately n=10.

Figure 2:
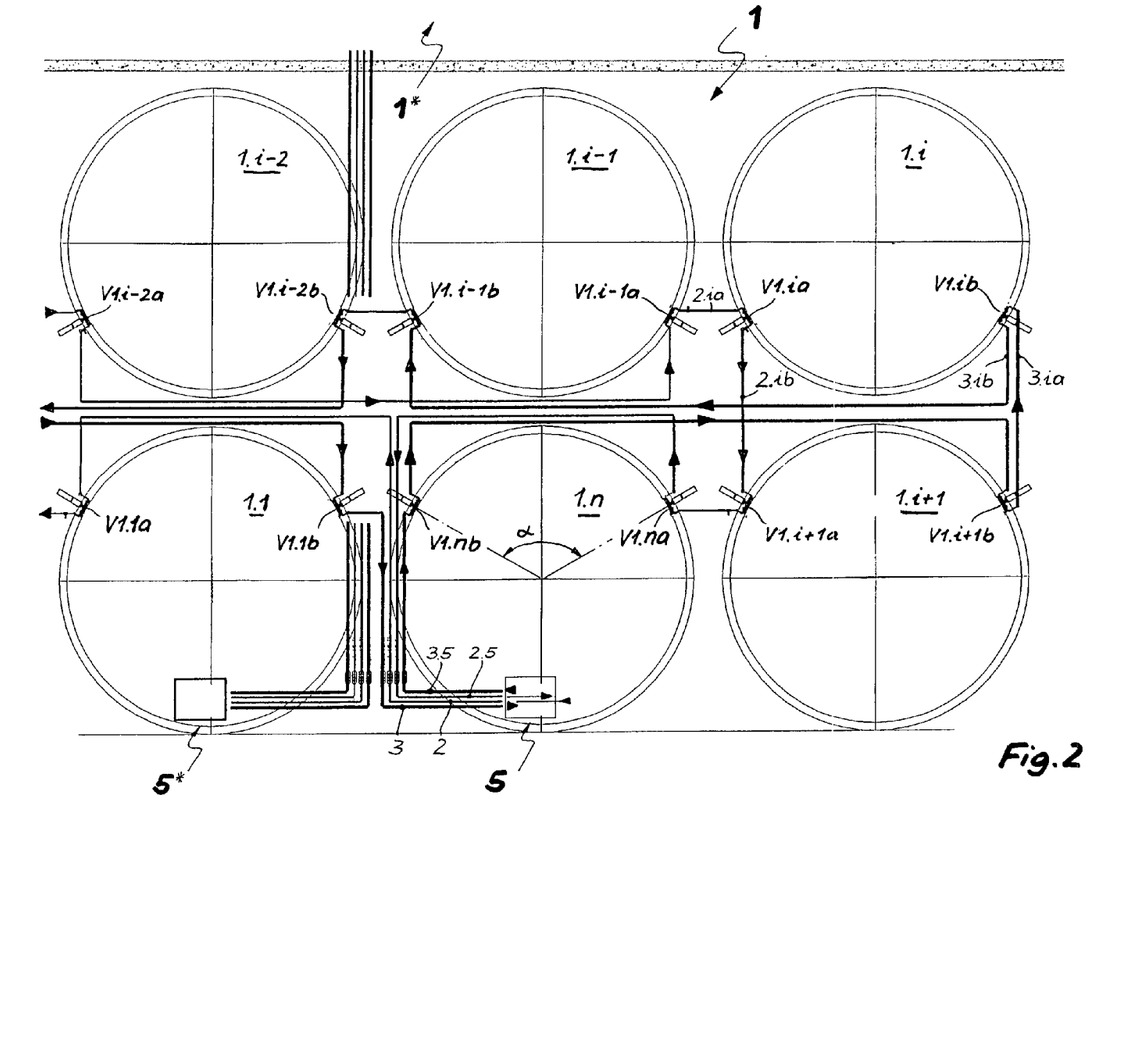
FIG. 2 shows a detail of a top view of a storage tank system according to FIG. 1, wherein the pertinent pipework with a central sampling device is illustrated more realistically than in FIG. 1.

FIG. 2 shows the actual pipework of the individual tanks 1.1 to 1.n while FIG. 1 only shows a schematic representation of the pipework in order to elucidate the function. In this case, n=5 tanks 1.1 to 1.n are illustrated in FIG. 1, wherein the third tank from the left carries the general designation 1.i and the adjacent tank on the right carries the general designation 1.i+1. FIG. 2 does not show the total number of tanks connected to the central sampling device 5. However, it elucidates that the tank 1.1 and the last tank 1.n are situated directly adjacent to one another in the present matrix-shaped arrangement of more than six tanks. The tanks situated in between carry the designations 1.i–2 to 1.i+1.

Each of the tanks 1.1 to 1.n (FIG. 1) contains a liquid product (fluid P to be sampled), of which a representative sample can be taken in the sampling device 5, if necessary. The pipework of the tanks 1.1 to 1.n that serves for filling and emptying the tanks is only indicated in the form of a short pipe section connected to the respective cone-shaped bottom section. A feed valve V1.1a, V1.2a, . . . , V1.ia, V1.i+1a, . . . , V1.na and a return valve V1.1b, V1.2b, . . . , V1.ib, V1.i+1b, . . . , V1.nb are respectively arranged on each tank 1.1 to 1.n in the lower region thereof, preferably on the cylindrical surface area and slightly above the cone-shaped bottom section, wherein said feed valves and return valves are positioned at a certain distance from one another on the assigned tank, are designed in a double-sealing fashion in the respective valve seat region, as well as in a mix-proof fashion, and feature valve seats that can be cleaned. For example, the above-described double-seat valve or double-seal valve or any comparable valve with the required properties may be considered for this purpose. Each of these feed and return valves V1.1a, V1.2a, . . . , V1.ia, V1.i+1a, . . . , V1.na and V1.1b, V1.2b, . . . , V1.ib, V1.i+1b, . . . , V1.nb respectively features a through-housing with a first and a second connecting sleeve a and b and a tank connection c that is connected to the interior of the respectively assigned tank 1.1 to 1.n and can be switched by means of the assigned feed or return valve.

A pipe system 4 for supplying cleaning fluids is assigned to the storage tank system 1, wherein said pipe system comprises a first line 4.1 for supplying a cleaning medium RM (so-called cleaning medium feed RV), a second line 4.2 for carrying off the cleaning medium RM (so-called cleaning medium return RR), a third line 4.3 for supplying desalinated water EW, a fourth line 4.4 for supplying steam D or hot water HW and a fifth line 4.5 for supplying sterile air SL. The lines 4.1 and 4.3 to 4.5 are connected to a feed line 2 by means of remote-controlled valves V4.1 to V4.4 while a return line 3 is connected to the fifth line 4.5 by means of a fifth valve V4.5, to the fourth line 4.4 by means of a sixth valve V4.6 and to the second line 4.2 by means of a seventh valve V4.7. A first drain valve V4.8 is arranged between the sixth valve V4.6 and the seventh valve V4.7, wherein the return line 3 can be emptied into a first gully 4.6 by means of said drain valve.

A cleaning medium RM, desalinated water EW, steam D or hot water HW and sterile air SL are supplied to the automatic sampling arrangement according to the invention, if necessary, via the above-described pipe system 4 in order to carry out a so-called CIP- or SIP-treatment (CIP: cleaning in place; SIP: sterilization in place). The fluids to be considered are carried off from the arrangement via the second line 4.2, the cleaning medium return RR or the first gully 4.6.

The feed line 2 is connected to the first connecting sleeve a on the through-housing of the first feed valve V1.1$a$ provided on the first tank 1.1 and continues to the second feed valve V1.2$a$ on the second tank 1.2 via the second connecting sleeve b. The other tanks 1.$i$ to 1.$n$ are analogously connected to one another in series by means of the respectively assigned feed valves V1.$ia$, V1.$i$+1$a$ and V1.$na$. The tanks 1.1 to 1.$n$ also are respectively connected to one another in series by means of the return line 3 extending through the respective connecting sleeves a, b of the return valves V1.1$b$, V1.2$b$, ..., V1.$ib$, V1.$i$+1$b$, ..., V1.$nb$.

This actual pipework of the feed line 2 and the return line 3 with the matrix-shaped arrangement of tanks is illustrated in FIG. 2. According to this illustration, the feed and return valves V1.1$a$ to V1.$na$ and V1.1$b$ to V1.$nb$ are respectively arranged on the tanks in groups (see, for example, the feed valves V1.$i$−1$a$, V1.$ia$, V1.$i$+1$a$ and V1.$na$) such that a clearly arranged pipework results that is also optimized with respect to its length. One practical arrangement of the feed valve and the return valve V1.$na$, V1.$nb$ relative to one another is shown on the tank 1.$n$ and is characterized in that these valves are arranged relative to one another at a preferred angle of $\alpha$=120 degrees referred to a plane extending perpendicular to the longitudinal axis of the tank 1.$n$. Referred to the vertical direction, the feed valve V1.$na$ and the assigned return valve V1.$nb$ are arranged at the same height in the region of the cylindrical surface area or in the upper region of the cone-shaped bottom section of the tank 1.$n$. This preferred arrangement applies analogously to the other tanks.

The feed line and the return line 2, 3 are connected to one another by means of the sampling device 5 on their end that lies opposite of the pipe system 4 (FIG. 1) and thusly form a closed circular pipeline 2/3. Referred to the flow direction, the sampling device 5 features a conveying device 5.1, preferably a centrifugal pump, a flowmeter 5.2 such as, for example, an inductive flowmeter, a quality control device 5.3 such as, for example, a densimeter and/or a measuring device for determining the $O_2$- or $CO_2$-concentration, a sampling valve V5.1 and a second drain valve V5.2, by means of which the closed circular pipeline 2/3 can be emptied into a second gully 5.4. The section of the feed line 2 entering the sampling device 5 is referred to as inlet line 2.5 and the section of the return line 3 exiting the sampling device 5 is referred to as outlet line 3.5

The actual pipework according to FIG. 2 elucidates that the inlet line and the outlet line 2.5, 3.5 and the feed and return lines 2, 3 leading to the pipe system 4 extend out of the storage tank system 1 and to the central sampling device 5 in a bundled fashion. The corresponding pipework of a second storage tank system 1\* (not shown here) with a second sampling device 5\* assigned thereto is realized analogously. The two sampling devices 5, 5\* are preferably arranged in spatial vicinity to one another in order to achieve the simplest, most clearly arranged and user-friendliest sampling of the storage tank systems 1, 1\* possible.

A first feed shut-off valve V2.1 is arranged in the feed line 2 (FIG. 2) extending to the first feed valve V1.1$a$ and defines a first section 2.1$a$ of the feed line on the tank 1.1 between itself and the feed valve V1.1$a$. A feed shut-off valve V2.2 to V2.$n$ is respectively arranged in the other sections of the feed line 2, namely in the sections between the following feed valves V1.2$a$ to V1.$na$. The respective feed shut-off valve V2.2 to V2.$n$ consequently divides the assigned section of the feed line 2 that is situated between the adjacent feed valves V1.2$a$ to V1.$na$ into two sections. Between the feed valves V1.1$a$ and V1.2$a$, these consist of the second section 2.1$b$ of the feed line on the tank 1.1 and the first section 2.2$a$ of the feed line on the tank 1.2. Between the tanks 1.2 and 1.$i$, they consist of the sections 2.2$b$ and 2.$ia$, between the tanks 1.$i$ and 1.$i$+1, they consist of the sections 2.$ib$ and 2.$i$+1$a$, and between the tanks 1.$i$+1 and 1.$n$, they consist of the sections 2.$i$+1$b$ and 2.$na$.

A first return shut-off valve V3.1 is arranged in the return line 3 leading to the first return valve V1.1$b$ and defines a second section 3.1$b$ of the return line on the tank 1.1 between itself and the return valve V1.1$b$. A return shut-off valve V3.2 to V3.$n$ is respectively arranged in the other sections of the return line 3, namely in the sections between the following return valves V1.2$b$ to V1.$nb$. The respective return shut-off valve V3.2 to V3.$n$ consequently divides the assigned section of the return line 3 that is situated between the adjacent return valves V1.2$b$ to V1.$n$ into two sections. Between the return valves V1.1$b$ and V1.2$b$, these consist of the first section 3.1$a$ of the return line on the tank 1.1 and the second section 3.2$b$ of the return line on the tank 1.2. Between the tanks 1.2 and 1.$i$, they consist of the sections 3.2$a$ and 3.$ib$, between the tanks 1.$i$ and 1.$i$+1, they consist of the sections 3.$ia$ and 3.$i$+1$b$, and between the tanks 1.$i$+1 and 1.$n$, they consist of the sections 3.$i$+1$a$ and 3.$nb$.

The method for the automatic sampling in a storage tank system 1, the structure of which was described above with reference to FIGS. 1 and 2, as well as the preparatory and subsequent procedural steps, are carried out as described below. Prior to the respective sampling of one of the tanks 1.1 to 1.$n$, the entire sampling system that is exposed to a fluid P to be sampled during the course of any sampling is cleaned with a cleaning medium RM in a flow-through fashion or sterilized with steam D or hot water HW in a flow-through fashion or completely flooded with desalinated water EW or with sterile air SL regardless of the respective content of the tanks 1.1 to 1.$n$, wherein these fluids RM, D, HW, EW, SL are supplied via the pipe system 4 (FIG. 1).

Figure 3:
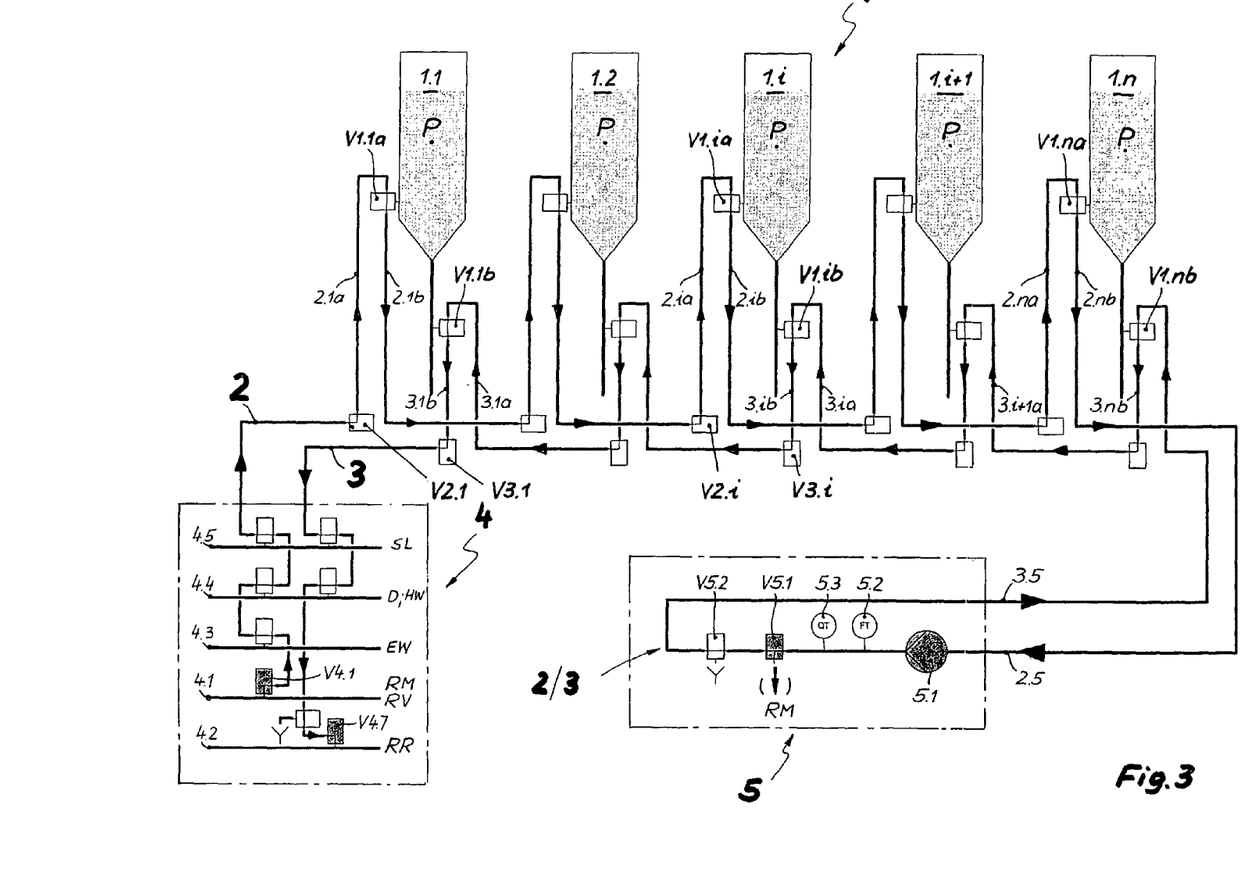
FIG. 3 shows a schematic representation of the arrangement according to FIG. 1, wherein the flow-through cleaning of the entire sampling system including the feed and return valves by means of the interconnected pipe system is illustrated in this figure.

FIG. 3 shows an example of the so-called CIP-cleaning with a cleaning medium RM. The cleaning medium RM is supplied via the first line 4.1 of the pipe system 4, namely the cleaning medium feed RV, is introduced into the feed line 2 by means of the first valve V4.1 and successively cleans all following sections 2.1$a$ to 2.$na$ downstream of the first feed shut-off valve V2.1 in connection with the respectively assigned sections 2.1$b$ to 2.5 of the feed line 2. The cleaning medium RM is introduced into the sampling device 5 through the inlet line 2.5, cleans its components 5.1, 5.2, 5.3, V5.1 and V5.2 therein while also subjecting the sample branch of the sampling valve V5.1 to a cleaning process (diverted RM) and then flows into the series-connected sections 3.$nb$ to 3.1$b$ in connection with the respectively assigned sections 3.$i$+1$a$ to 3.1$a$ of the return line 3 through the closed circular pipeline 2/3 and the output line 3.5 in order to be ultimately returned into the second line 4.2 of the pipe system 4, namely the cleaning medium return RR, via the return line 3 and the seventh valve V4.7 downstream of the first return shut-off valve V3.1.

The same above-described flow path is also used for cleaning the valve seat surfaces of the respective feed and return valves V1.1a to V1.na and V1.1b to V1.nb. This concerns the valve seat surface of the respective double-sealing feed and return valves that faces away from the interior of the respective tank 1.1 to 1.n because the invention should also make it possible to carry out a cleaning process while a tank is exposed to the product.

The SIP-treatment of the entire above-described sampling system with steam D or hot water HW or its exposure to desalinated water EW or sterile air SL is realized in an adequate fashion, wherein only the path to the corresponding source of the fluid D, HW, EW or SL, namely one of the lines 4.3 to 4.5, is released within the pipe system 4.

Figure 7:
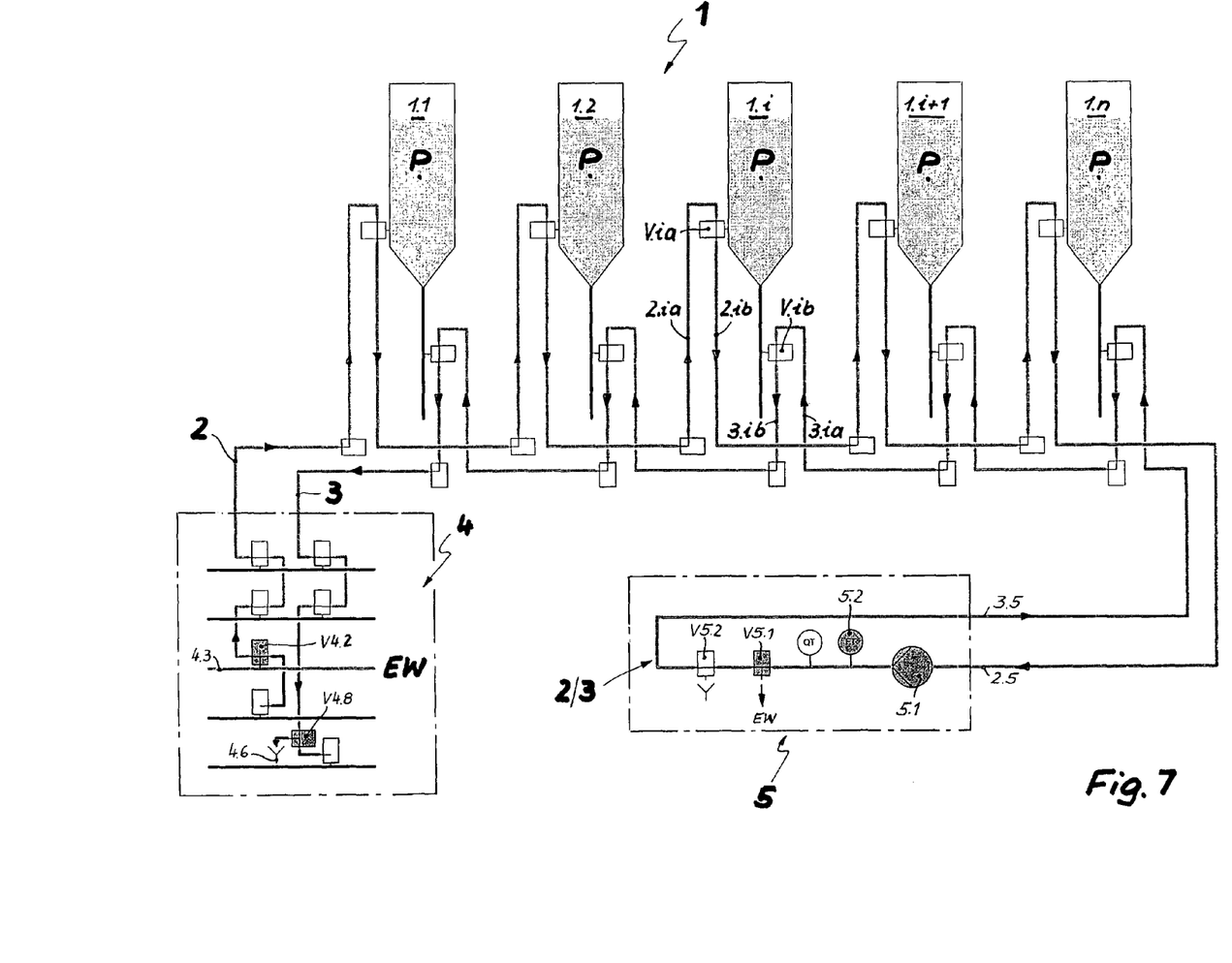
FIG. 7 shows a schematic representation of the arrangement according to FIG. 1, wherein the entire sampling system including the feed and return valves are exposed to desalinated water in this figure via the connected pipe system in order to supply cleaning fluids.

FIG. 7 shows an example of the above-described option of exposing the entire sampling system to desalinated water EW. A corresponding exposure is carried out prior to a sampling of a selected tank 1.1 to 1.n in order to create flawless and unambiguous starting conditions for a representative sampling. The desalinated water EW is introduced into the feed line 2 and its following sections via the third line 4.3 and the second valve V4.2 and is drained into the first gully 4.6 via the closed circular pipeline 2/3 and the sampling device 5 on its path through the sections of the return line 3 and the latter itself and on its path through the first drain valve V4.8. In order to maintain the ejection losses of desalinated water EW into the first gully 4.6 at a minimum, the exposure of the entire sampling system to desalinated water EW is controlled by means of the flowmeter 5.2.

Figure 4:
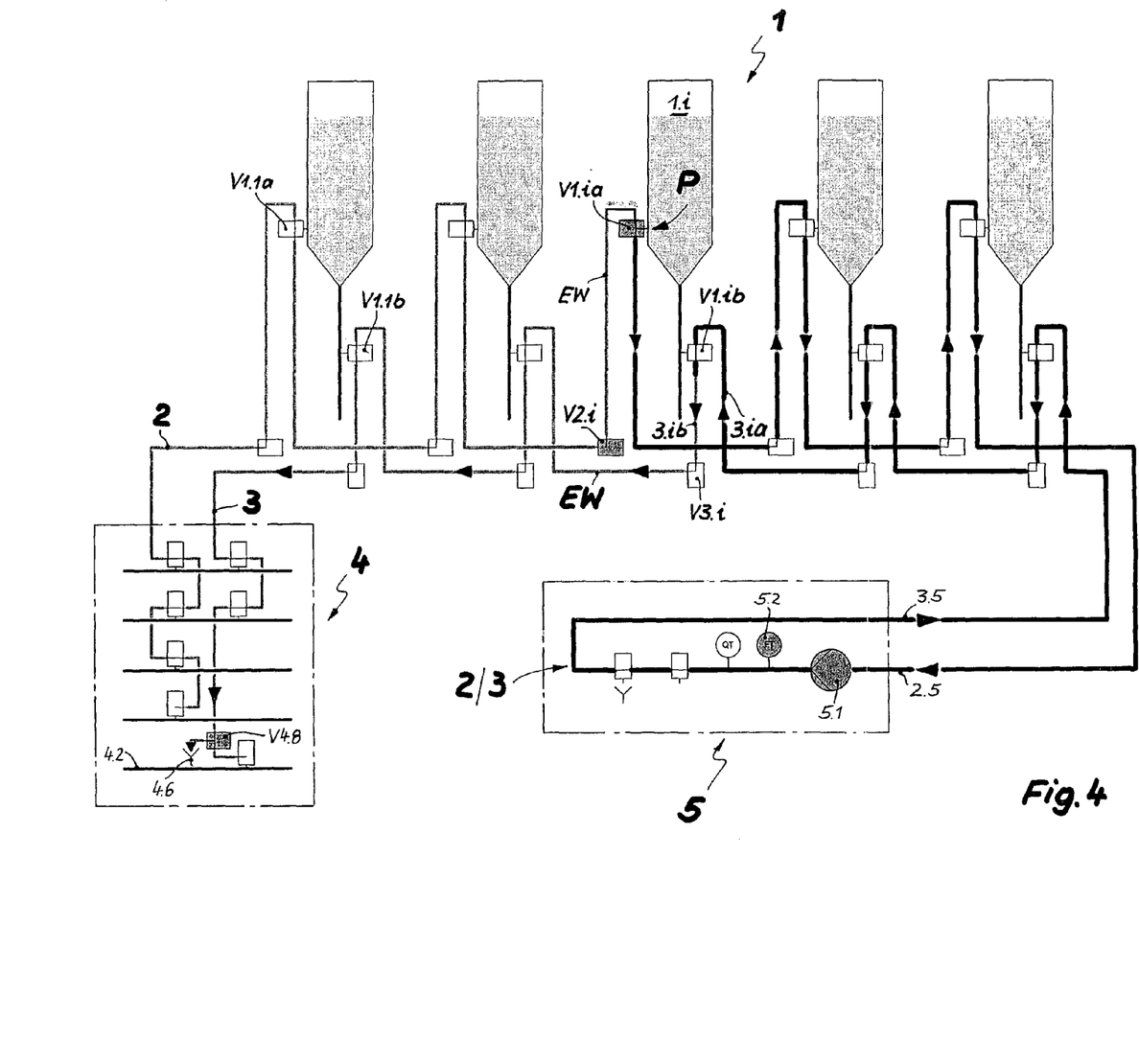
FIG. 4 shows a schematic representation of the arrangement according to FIG. 1, wherein the ejection of the desalinated water from the pipeline region that is subsequently used for the sampling of the selected tank is illustrated in this figure.

Prior to the sampling, for example, on the tank 1.i, the entire sampling system is completely exposed to desalinated water EW (FIG. 4). In order to carry out the sampling (see FIG. 5), it is initially necessary to completely eject the desalinated water EW from the sections of the feed line 2 and the sections of the return line 3 including the closed circular pipeline 2/3 in the region between the feed valve V1.ia and the return valve V1.ib (pipelines concerned are illustrated with thick lines). This ejection is realized by means of the fluid P to be sampled that is diverted from the tank 1.i to be sampled at a first location, at which the feed valve V1.ia is connected to the tank 1.i, namely into the first gully 4.6 via the sections of the return line 3 situated downstream of the return valve V1.ib. In this case, the feed shut-off valve V2.i is closed and the other downstream feed shut-off valves V2.i+1 and V2.n referred to the flow direction are opened. The return shut-off valve V3.i and all other return shut-off valves are opened. The ejection is controlled very precisely by means of the flowmeter 5.2 in the sampling device 5.

The prerequisites for a representative sampling of the selected tank 1.i are now fulfilled. The sampling of another tank such as, for example, the first tank 1.1 requires a corresponding ejection of the desalinated water EW from the concerned sections of the feed line and the return line 2, 3 between the feed valve V1.1a and the return valve V1.1b.

Figure 5:
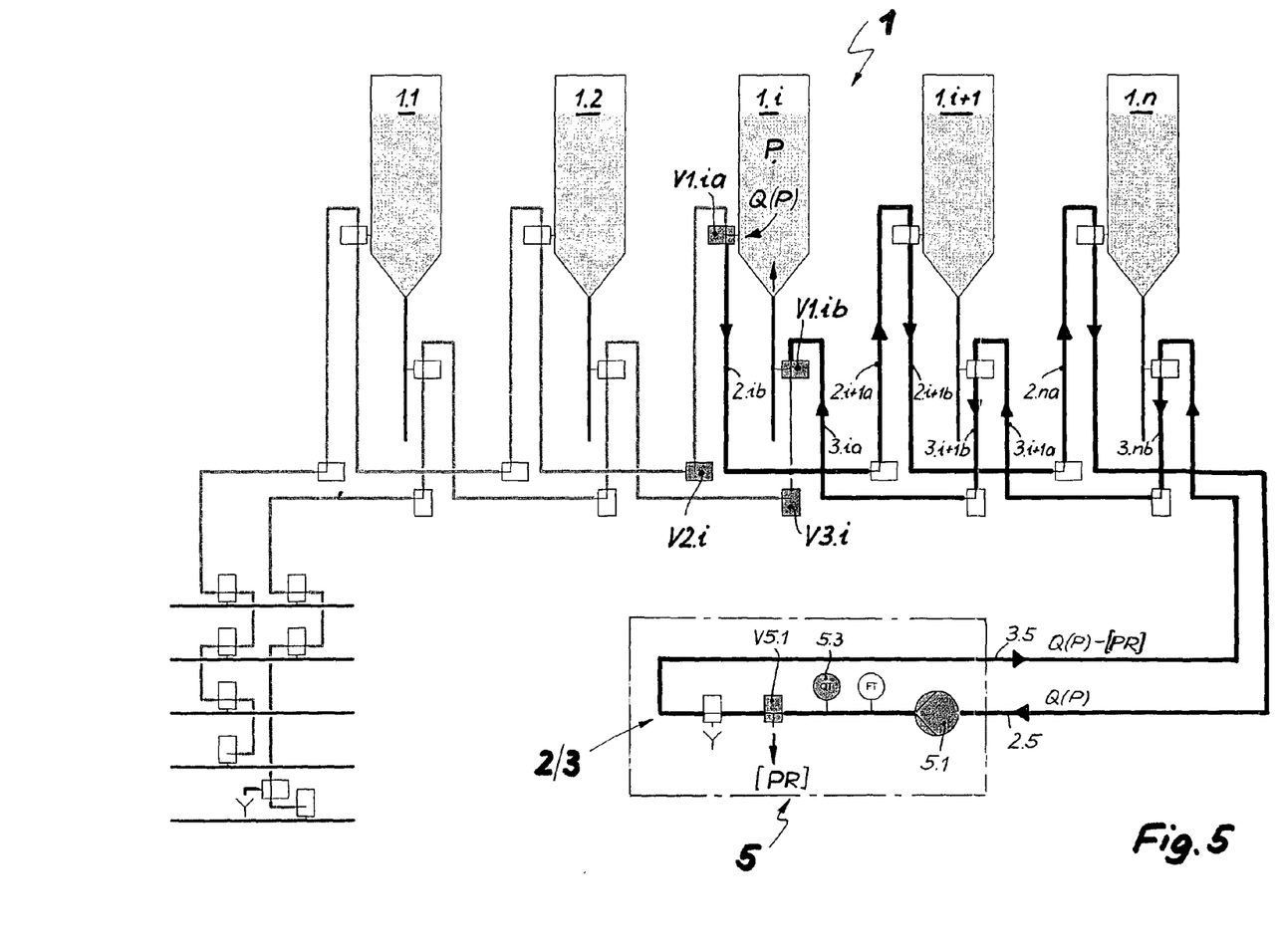
FIG. 5 shows a schematic representation of the arrangement according to FIG. 1, wherein the sampling of the selected tank is illustrated in this figure.

After the ejection of the desalinated water EW from the concerned region and its substitution with the fluid P to be sampled, a volume flow Q(P) of the fluid P to be sampled is automatically diverted from the selected tank 1.i at the first location by means of the feed valve V1.ia (FIG. 5).

This volume flow Q(P) is fed to the sampling device 5 via the sections 2.ib and 2.i+1b in connection with the sections 2.i+1a and 2.na and the inlet line 2.5 and is returned from the sampling device into the selected tank 1.i via the outlet line 3.5 and the sections 3.nb and 3.i+1b in connection with the sections 3.i+1a and 3.ia at a second location, to which the return valve V1.ib is connected. The concerned pipelines for the circulation are illustrated with thick lines. Within the sampling device 5, a quality control of the fluid P to be sampled is carried out in a flow-through fashion by means of the device 5.3 during the circulation of the volume flow Q(P) from the first to the second location and/or a sample quantity PR of the fluid P is diverted from the volume flow Q(P) by means of the sampling valve V5.1 such that the volume flow of the fluid Q(P) to be sampled minus the diverted sample quantity PR, namely the volume flow Q(P)–PR, flows back via the outlet line 3.5.

Figure 6:
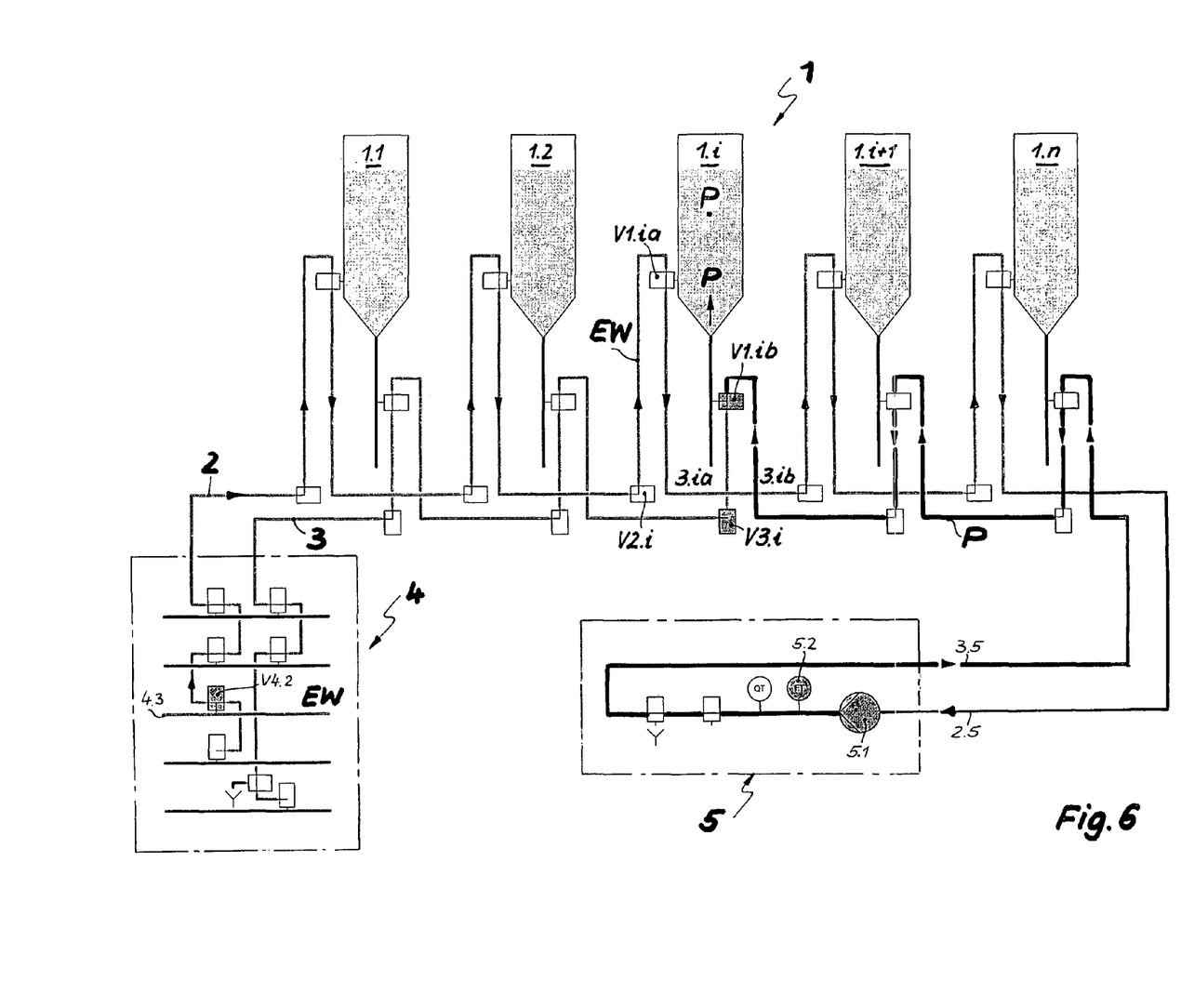
FIG. 6 shows a schematic representation of the arrangement according to FIG. 1, wherein the lossless ejection of the sampled fluid into the tank selected for sampling is illustrated in this figure.

After the respective sampling of one of the selected tanks 1.1 to 1.n, namely the tank 1.i (FIG. 6) in the described embodiment, the sampled fluid P situated in the assigned region for the circulation of the volume flow Q(P) of the sampled fluid P is completely ejected out of this region into the sampled tank 1.1 to 1.n, namely the tank 1.i in the described embodiment, at the second location by means of the desalinated water EW. In order to achieve this, the return valve V1.ib on the tank 1.i remains opened and the feed valve V1.ia is closed. The return shut-off valve V3.i remains closed while the feed shut-off valve V2.i is opened. All other feed and return shut-off valves remain open. The desalinated water EW is supplied via the third line 4.3 and the second valve V4.2. The ejection is once again precisely controlled by means of the flowmeter 5.2. This demonstrates that the sampling takes place without noteworthy loss of fluid P to be sampled. During the course of the sampling, the loss is limited at best to the quantities that need to be ordinarily provided for the return into the tank 1.i for safety reasons during the ejection of the sampled fluid P by means of desalinated water EW because the fluid change-over P/EW is not highly selective.

LIST OF REFERENCE SYMBOLS FOR THE ABBREVIATIONS USED

1 Storage tank system
1* Second storage tank system
1.1 to 1.n Tank (tank 1.1, 1.2, . . . , 1.i–2, 1.i–1, 1.i, 1.i+1, . . . , 1.n)
1.i One of the tanks 1.1 to 1.n
2 Feed line
2.1a First section of the feed line on the tank 1.1
2.2a First section of the feed line on the tank 1.2
2.ia First section of the feed line on the tank 1.i
2.ia+1 First section of the feed line on the tank 1.i+1
2.na First section of the feed line on the tank 1.n
2.1b Second section of the feed line on the tank 1.1
2.2b Second section of the feed line on the tank 1.2
2.ib Second section of the feed line on the tank 1.i
2.i+1b Second section of the feed line on the tank 1.i+1
2.5 Inlet line (into sampling device 5)
2/3 Closed circular pipeline
3 Return line
3.1a First section of the return line on the tank 1.1
3.2a First section of the return line on the tank 1.2
3.ia First section of the return line on the tank 1.i
3.i+1a First section of the return line on the tank 1.i+1
3.1b Second section of the return line on the tank 1.1
3.2b Second section of the return line on the tank 1.2
3.ib Second section of the return line on the tank 1.i
3.i+1b Second section of the return line on the tank 1.i+1
3.nb Second section of the return line on the tank 1.n 3.5 Outlet line (from sampling device 5)
4 Pipe system for supplying cleaning fluids
4.1 First line (feed RV for cleaning medium RM)
4.2 Second line (return RR for cleaning medium RM)
4.3 Third line (for desalinated water—EW)
4.4 Fourth line (for steam—D or hot water—HW)
4.5 Fifth line (for sterile air—SL)
4.6 First gully
5 Sampling device
5* Second sampling device
5.1 Conveying device
5.2 Flowmeter
5.3 Quality control device (e.g., density, $O_2$-concentration)
5.4 Second gully
α Relative angle
D Steam
EW Desalinated water
HW Hot water
Q(P) Volume flow of the fluid P to be sampled
Q(P)–PR Volume flow of the fluid P to be sampled minus the diverted sample quantity PR
P Fluid (product) to be sampled or sampled fluid
PR Sample quantity
RM Cleaning medium
RR Cleaning medium return
RV Cleaning medium feed
SL Sterile air
Valves
Valves in the Sampling Device 5
V5.1 Sampling valve
V5.2 Second drain valve
Valves in the Feed Line 2
V1.1a First feed valve (can be automatically actuated, is mix-proof and features valve seats that can be cleaned ([*]))
V1.2a Second feed valve ([*])
V1.ia i-th feed valve ([*])
V1.i+1a i-th+1 feed valve ([*])
V1.na n-th feed valve ([*])
V2.1 First feed shut-off valve
V2.2 Second feed shut-off valve
V2.i i-th feed shut-off valve
V2.i+1 i-th+1 feed shut-off valve
V2.n n-th feed shut-off valve
Valves in the Return Line 3
V1.1b First return valve (can be automatically actuated, is mix-proof and features valve seats that can be cleaned ([*]))
V1.2b Second return valve ([*])
V1.ib i-th return valve ([*])
V1.i+1b i-th+1 return valve ([*])
V1.nb n-th return valve ([*])
V3.1 First return shut-off valve
V3.2 Second return shut-off valve
V3.i i-th return shut-off valve
V3.i+1 i-th+1 return shut-off valve
V3.n n-th return shut-off valve
a First connecting sleeve
  (on the through-housing of the feed or return valve)
b Second connecting sleeve
  (on the through-housing of the feed or return valve)
c (Switchable) tank connection (on the feed or return valve)
Valves and the Pipe System 4
V4.1 First valve
V4.2 Second valve
V4.3 Third valve
V4.4 Fourth valve
V4.5 Fifth valve
V4.6 Sixth valve
V4.7 Seventh valve
V4.8 First drain valve

The invention claimed is:

1. An arrangement for the automatic sampling in a storage tank system interconnected to a pipe system for supplying cleaning fluids, the storage tank system comprising several tanks and a sampling device that is respectively associated with all tanks via permanent pipework, wherein a feed valve and a return valve are respectively arranged on each tank in the lower region thereof and said feed and return valves are positioned at a certain distance from one another, are designed in a double-sealing fashion in their respective valve seat region, as well as in a mix-proof fashion, and feature valve seats that can be cleaned, wherein each of these feed and return valves features a through-housing with a first and a second connecting sleeve and a tank connection that is connected to the interior of the respectively assigned tank and can be switched by means of the assigned valve, wherein the storage tank system is respectively connected to the pipe system via a feed line and a return line, wherein the tanks are respectively connected to one another in series by means of the feed line extending through the respective connecting sleeves of the feed valves and by means of the return line extending through the respective connecting sleeves of the return valves, wherein the feed line and the return line are connected to one another by means of a sampling device on their end that lies opposite of the pipe system and form a closed circular pipeline, wherein one feed shut-off valve is respectively provided that is arranged in each first section of the feed line that is situated upstream of the feed valve referred to the flow direction, and wherein one return shut-off valve is respectively provided that is arranged in each second section of the return line that is situated downstream of the return valve referred to the flow direction.

2. The arrangement according to claim 1,
   wherein the feed valve and the return valve are respectively realized in the form of a double-seat valve with a first closing element in the form of a sliding piston that is situated adjacent to the tank connection and with a second closing element that is realized in the form of a valve seat disk, wherein the two closing elements control a connecting opening between the tank connection and the through-housing that accommodates the two connecting sleeves, and both closing elements, in the closed position of the double-seat valve as well as in its open position, between one another define a leakage cavity that is connected to the surroundings of the double-seat valve via at least one connecting path wherein the first closing element comes in contact with the second closing element during the course of the opening movement of the double-seat valve and also transfers this second closing element into the open position, wherein the opening movement is directed away from the tank, and wherein the first closing element can be transferred into a partially open position by means of a first partial stroke that is directed opposite to the opening movement and the second closing element can be transferred into a partially open position by means of a second partial stroke that is directed in the same direction as the opening movement in order to clean the respective valve seat.

3. The arrangement according to claim 1,
   wherein the feed valve and the return valve are respectively realized in the form of a double-seal valve with a closing element in the form of a sliding piston that cooperates with a cylindrical valve seat surface by means of two sealing points that are axially spaced apart from one another, wherein the cylindrical valve seat surface borders a connecting opening that connects the tank connection to the through-housing accommodating the two connecting sleeves and the connecting opening is controlled by the closing element, wherein a leakage cavity that is connected to the surroundings of the double-seal valve via at least one connecting path is formed between the sealing points, and wherein a partial stroke of the closing element either exposes one or the other sealing point in order to clean the respective valve seat.

4. The arrangement according to claim 1,
wherein the pipe system features a first line for supplying a cleaning medium, a second line for carrying off the cleaning medium, a third line for supplying desalinated water, a fourth line for supplying steam or hot water and a fifth line for supplying sterile air.

5. The arrangement according to claim 1,
wherein the sampling device features a conveying device and a sampling valve referred to the flow direction.

6. The arrangement according to claim 5,
wherein a flowmeter and a quality control device are arranged between the conveying device and the sampling valve referred to the flow direction.

7. The arrangement according to claim 1,
wherein the feed valve and the respectively assigned return valve are arranged at the same height in the region of the cylindrical surface area or in the upper region of the cone-shaped bottom section of the corresponding tank.

8. The arrangement according to claim 7,
wherein the feed valve and the respectively assigned return valve are arranged relative to one another at an angle of $90 \leqq \alpha \leqq 180$ degrees, preferably at $\alpha=120$ degrees, referred to a plane extending perpendicular to the longitudinal axis of the tank.

9. The arrangement according to claim 2,
wherein a connecting path between the leakage cavity of the feed valve and its surroundings is designed for obtaining a manual sample.

10. A method for the automatic sampling in a storage tank system interconnected to a pipe system for supplying cleaning fluids, with a storage tank system comprising several tanks and a sampling device that is respectively associated with all tanks via permanent pipework, wherein an automatic sampling arrangement according to claim 1 is used, wherein a volume flow of the fluid to be sampled is automatically diverted from a selected tank at a first location, wherein this volume flow is fed to the sampling device and is returned from the sampling device into the selected tank at a second location, and wherein a quality control of the fluid to be sampled is carried out in a flow-through fashion and/or a sample quantity of the fluid to be sampled is diverted from the volume flow within the sampling device during the circulation of the volume flow from the first location to the second location.

11. The method according to claim 10,
wherein the entire sampling system that is exposed to the fluid to be sampled during the course of any sampling is cleaned with a cleaning medium in a flow-through fashion or sterilized with steam or hot water in a flow-through fashion or completely flooded with desalinated water or with sterile air prior to the respective sampling of one of the tanks regardless of the respective content of the tanks, wherein these fluids are supplied via the pipe system.

12. The method according to claim 11,
wherein the desalinated water situated in the assigned region for the circulation of the volume flow of the fluid to be sampled is ejected out of this region into the pipe system by means of the fluid to be sampled prior to the respective sampling of one of the selected tanks, wherein the fluid to be sampled is diverted from the tank to be sampled at the first location.

13. The method according to claim 10,
wherein the sampled fluid situated in the assigned region for the circulation of the volume flow of the sampled fluid is completely ejected out of this region into the sampled tank by means of the desalinated water at the second location subsequent to the respective sampling of one of the selected tanks.

14. The method according to claim 12,
wherein the ejections of the desalinated water or the sampled fluid are controlled by means of a flowmeter provided in the region of the circulating volume flow.

15. The method according to claim 13,
wherein the ejections of the desalinated water or the sampled fluid are controlled by means of a flowmeter provided in the region of the circulating volume flow.

* * * * *